US012558343B2

(12) United States Patent
Zhang et al.

(10) Patent No.: US 12,558,343 B2
(45) Date of Patent: Feb. 24, 2026

(54) MEDICAL USE OF ICARITIN

(71) Applicant: Lunan Pharmaceutical Group Corporation, Linyi (CN)

(72) Inventors: Guimin Zhang, Linyi (CN); Jingchun Yao, Linyi (CN); Chenghong Sun, Linyi (CN); Bin Li, Linyi (CN); Sina Pan, Linyi (CN)

(73) Assignee: Lunan Pharmaceutical Group Corporation, Linyi (CN)

( * ) Notice: Subject to any disclaimer, the term of this patent is extended or adjusted under 35 U.S.C. 154(b) by 774 days.

(21) Appl. No.: 17/909,921

(22) PCT Filed: Mar. 9, 2021

(86) PCT No.: PCT/CN2021/079791
§ 371 (c)(1),
(2) Date: Sep. 7, 2022

(87) PCT Pub. No.: WO2021/180087
PCT Pub. Date: Sep. 16, 2021

(65) Prior Publication Data
US 2023/0103858 A1 Apr. 6, 2023

(30) Foreign Application Priority Data

| Mar. 10, 2020 | (CN) | .......................... | 202010163055.X |
| Mar. 10, 2020 | (CN) | .......................... | 202010163671.5 |
| Mar. 10, 2020 | (CN) | .......................... | 202010163672.X |
| Mar. 10, 2020 | (CN) | .......................... | 202010163676.8 |
| Mar. 10, 2020 | (CN) | .......................... | 202010163677.2 |

(51) Int. Cl.

| *A61P 7/04* | (2006.01) |
| *A61K 9/00* | (2006.01) |
| *A61K 9/107* | (2006.01) |
| *A61K 9/20* | (2006.01) |
| *A61K 9/48* | (2006.01) |
| *A61K 31/352* | (2006.01) |
| *A61K 31/4365* | (2006.01) |
| *A61K 31/616* | (2006.01) |
| *A61K 31/727* | (2006.01) |
| *A61K 38/48* | (2006.01) |
| *A61K 38/49* | (2006.01) |
| *A61K 47/10* | (2017.01) |
| *A61K 47/26* | (2006.01) |
| *A61K 47/44* | (2017.01) |
| *A61P 1/00* | (2006.01) |

(52) U.S. Cl.
CPC .......... *A61K 31/352* (2013.01); *A61K 9/0019* (2013.01); *A61K 9/1075* (2013.01); *A61K 9/2018* (2013.01); *A61K 9/2031* (2013.01); *A61K 9/2054* (2013.01); *A61K 9/4825* (2013.01); *A61K 9/4858* (2013.01); *A61K 9/4866* (2013.01); *A61K 9/4875* (2013.01); *A61K 9/4891* (2013.01); *A61K 31/4365* (2013.01); *A61K 31/616* (2013.01); *A61K 31/727* (2013.01); *A61K 38/48* (2013.01); *A61K 38/482* (2013.01); *A61K 38/49* (2013.01); *A61K 47/10* (2013.01); *A61K 47/26* (2013.01); *A61K 47/44* (2013.01); *A61P 1/00* (2018.01); *A61P 7/04* (2018.01); *C12Y 304/00* (2013.01); *C12Y 304/21031* (2013.01); *C12Y 304/21068* (2013.01)

(58) Field of Classification Search
CPC .............. A61K 31/352; A61K 31/4365; A61K 31/616; A61K 31/727; A61K 38/48; A61K 38/482; A61K 38/49; A61K 47/10; A61K 47/26; A61K 9/0019; A61K 9/1075; A61K 9/20; A61K 9/48; A61K 9/4891; A61K 9/4875; A61P 7/04; A61P 1/00
See application file for complete search history.

(56) References Cited

U.S. PATENT DOCUMENTS

| 6,399,579 B1 | 6/2002 | Lenoble et al. | |
| 2016/0250243 A1* | 9/2016 | Zhao ................... | A61K 9/0019 424/85.2 |
| 2020/0115358 A1 | 4/2020 | Wei et al. | |

FOREIGN PATENT DOCUMENTS

| CN | 1460482 A | 12/2003 |
| CN | 101574339 A | 11/2009 |
| CN | 101637466 A | 2/2010 |
| CN | 101637467 A | 2/2010 |
| CN | 103690524 A | 4/2014 |
| CN | 104546822 A | 4/2015 |
| CN | 104546823 A | 4/2015 |
| CN | 105963293 A | 9/2016 |

(Continued)

OTHER PUBLICATIONS

Segawa et al., Isolation of blood platelet aggregation inhibitor from Epimedium grandiflorum MORR. The Meiji University Agricultural Department Report of Research. 1991;90:13-16.

(Continued)

*Primary Examiner* — Sarah Pihonak
*Assistant Examiner* — Padmaja S Rao
(74) *Attorney, Agent, or Firm* — McCarter & English, LLP; Yu Lu

(57) ABSTRACT

The present disclosure provides use of icaritin in preparing a drug for preventing and treating a bleeding disorder and belongs to the field of medicine. The icaritin can relieve platelet dysfunction, shorten thromboplastin time, and promote blood coagulation, and can be used for preventing and treating the bleeding disorder, especially for treating hemorrhagic transformation after cerebral infarction, gastrointestinal bleeding caused by a thrombolytic or antithrombotic drug for cerebral infarction, or a bleeding complication of a thrombolytic or antithrombotic drug for myocardial infarction.

20 Claims, No Drawings

(56)                    References Cited

FOREIGN PATENT DOCUMENTS

| CN | 109369748 A | 2/2019 |
| EP | 2808016 A1 | 12/2014 |
| EP | 3061452 A1 | 8/2016 |
| JP | 2016-534074 A | 11/2016 |
| JP | 2019-507796 A | 3/2019 |

OTHER PUBLICATIONS

Sun et al., Icaritin Improves Antibody-Induced Thrombocytopenia in a Mouse Model by Regulating T-cell Polarization. Planta Med. Feb. 2018;84(3):168-175.

Callaghan et al., Novel therapeutics for hemophilia and other bleeding disorders. Blood. Jul. 5, 2018;132(1):23-30.

Kritharis et al., Hereditary hemorrhagic telangiectasia: diagnosis and management from the hematologist's perspective. Haematologica. Sep. 2018;103(9):1433-1443.

Piran et al., Treatment of bleeding complications in patients on anticoagulant therapy. Blood. Jan. 31, 2019;133(5):425-435.

Saes et al., Hemorrhagic disorders of fibrinolysis: a clinical review. J Thromb Haemost. May 30, 2018;16:1498-1509.

Yasuda et al., Treatment and prevention of gastrointestinal bleeding in patients receiving antiplatelet therapy. World J Crit Care Med. Feb. 4, 2015;4(1):40-6.

Zhang et al., Hemorrhagic transformation after cerebral infarction: current concepts and challenges. Ann Transl Med. Aug. 2014;2(8):81, 7 pages.

Du et al., Evaluation of the Therapeutic Effect of a Flavonoid Prescription against Rabbit Hemorrhagic Disease In Vivo. Biomed Res Int. Apr. 4, 2019;2019:5201790, 10 pages.

Li et al., Epimedium decoction, polysaccharides and crude flavonoids effects on platelet aggregation in rats. Chinese Journal Chinese Materia Medica. Aug. 31, 1987;12(8):40-42, 64.

Li, Icariin mitigates intracranial hemorrhage of zebra fish induced by atorvastatin. Journal of Zunyi Medical University. Apr. 2014;37(2):181-187.

Yao et al., Icaritin, an exogenous phytomolecule, enhances osteogenesis but not angiogenesis—an in vitro efficacy study. PLoS One. 2012;7(8):e41264, 10 pages.

Ye et al., The effect of icariin on platelet activation and its molecular mechanism. Zhejiang Journal of Traditional Chinese Medicine Aug. 2013;48(8):609-611.

International Search Report and Written Opinion for Application No. PCT/CN2021/079791, dated Jun. 8, 2021, 21 pages.

* cited by examiner

MEDICAL USE OF ICARITIN

REFERENCE TO RELATED APPLICATIONS

This application is a U.S. national stage application filed under 35 U.S.C. § 371 based on International Patent Application No. PCT/CN2021/079791, filed on Mar. 9, 2021, which in turn claims foreign priority and the benefit of the filing dates of Chinese Patent Application No. 202010163055.X, filed on Mar. 10, 2020, Chinese Patent Application No. 202010163671.5, filed on Mar. 10, 2020, Chinese Patent Application No. 202010163672.X, filed on Mar. 10, 2020, Chinese Patent Application No. 202010163676.8, filed on Mar. 10, 2020, and Chinese Patent Application No. 202010163677.2, filed on Mar. 10, 2020. The entire contents of each of the above applications are incorporated herein by reference.

FIELD OF TECHNOLOGY

The present disclosure belongs to the field of medicine, and relates to medical use of icaritin, in particular to the use in preparing a drug for preventing or treating a bleeding disorder.

BACKGROUND

When a human blood vessel is injured, blood can flow out or seep out of the blood vessel. At this time, the body will stop bleeding through a series of physiological reactions and the process is called hemostasis. The hemostasis involves a variety of factors and a series of complex physiological and biochemical reactions. Bleeding disorders are characterized by spontaneous bleeding or continuous bleeding after vascular injury due to defective hemostatic functions.

The bleeding disorders can be classified into the following main types according to etiology and pathogenesis. (I) Caused by platelet dysfunction. The bleeding disorders comprise hemorrhagic transformation after cerebral infarction, gastrointestinal bleeding caused by thrombolytic or antithrombotic drugs for cerebral infarction, or bleeding complications of thrombolytic or antithrombotic drugs for myocardial infarction. The hemorrhagic transformation after cerebral infarction is secondary, primary or asymptomatic hemorrhagic transformation after ischemic cerebral infarction. A thrombolytic drug or anticoagulant drug treatment is effective for treating acute ischemic infarction at present, but can also cause various serious complications such as hemorrhagic transformation and the like while dissolving thrombus, and therefore, the clinical application of the treatment is seriously limited. At present, western medicine only prevents and treats various complications after the thrombolytic drug or anticoagulant drug treatment from each single link or single factor, and does not obtain a satisfactory curative effect. Therefore, it is very important to fully exert advantages of traditional Chinese medicines in integral regulation and multi-link comprehensive treatment and find an effective treatment method and a prescription capable of relieving or eliminating various bleeding transformation risks while dissolving thrombus to improve short-term and long-term curative effects of thrombolytic treatment of infarction diseases. (II) Caused by vessel wall abnormalities. The vessel wall abnormalities are congenital or genetic and acquired. The congenital vessel wall abnormalities comprise hereditary hemorrhagic telangiectasia; familial purpura simplex and congenital connective tissue disease. (III) Caused by coagulation abnormalities. The coagulation abnormalities are congenital or genetic and acquired. The congenital coagulation abnormalities refer to hemophilia A and B and hereditary FXI deficiency, hereditary prothrombin, FV, FVII and FX deficiencies, hereditary fibrinogen deficiency and hypofibrinogenemia, hereditary FXII deficiency and hypofunction. The hereditary coagulation abnormalities refer to coagulation disorders in liver disease, vitamin K deficiency, formation of anti-factor VIII and IX antibodies, coagulation disorders in uremia, etc. (IV) Caused by anticoagulation and fibrinolysis abnormalities. The bleeding disorders are mainly acquired and caused by factors including but not limited to heparin overuse, coumarin overdose, increased immune-related anticoagulants or overdose of thrombolytic drugs.

*Herba epimedii* is dry stems and leaves of *Epimedium brevicornum* Maxim., *Epimedium sagittatum* Maxim., *Epimedium pubescens* Maxim. or *Epimedium koreanum* Nakai. The *herba epimedii* is mainly used for treating kidney-yang deficiency, impotence, frequent micturition and infertility, rheumatism pain, numbness and contracture of limbs, flaccidity of muscles and bones, difficulty in walking, dyspnea with cough and shortness of breath clinically.

Icaritin (IT) is a polyhydroxy flavonoid monomer component in *Epimedium brevicornu* belonging to *Epimedium* of *Berberidaceae*. Pharmacological researches show that the icaritin has a stronger osteoporosis resisting effect than other flavonoid glycoside compounds in *herba epimedii* and has effects on promoting osteoblast activity and inhibiting osteoclast activity in vitro. Icariin and icaritin, as important active ingredients in *herba epimedii*, are receiving more attention from medical workers in recent years. For example, patent application CN101637467A discloses use of icaritin in preparing a drug for treating osteoporosis. U.S. Pat. No. 6,399,579 discloses use of icaritin in treating sexual dysfunction.

SUMMARY

During a study, the applicant finds that icaritin can relieve platelet dysfunction, shorten thromboplastin time, and promote blood coagulation, and can be used for preventing and treating platelet dysfunction and a bleeding disorder caused thereby, a bleeding disorder caused by coagulation abnormalities, a bleeding disorder caused by vessel wall abnormalities or a bleeding disorder caused by anticoagulation and fibrinolysis abnormalities.

In one aspect, the present application provides use of icaritin in preparing a drug for preventing or treating a disease, wherein the disease is platelet dysfunction and a bleeding disorder caused thereby, a bleeding disorder caused by coagulation abnormalities, a bleeding disorder caused by vessel wall abnormalities or a bleeding disorder caused by anticoagulation and fibrinolysis abnormalities.

In one embodiment, the bleeding disorder caused by the platelet dysfunction is selected from the group consisting of hemorrhagic transformation after cerebral infarction, gastrointestinal bleeding caused by a thrombolytic or antithrombotic drug for cerebral infarction, or a bleeding complication of a thrombolytic or antithrombotic drug for myocardial infarction.

In one embodiment, the hemorrhagic transformation after cerebral infarction is secondary, primary or asymptomatic hemorrhagic transformation after ischemic cerebral infarction.

In one embodiment, the secondary hemorrhagic transformation is caused by using one or more treatment methods of a thrombolytic drug, an antithrombotic drug and endovascular therapy.

In one embodiment, the thrombolytic drug is selected from the group consisting of urokinase, streptokinase, reteplase, alteplase, tenecteplase and lanoteplase. In one embodiment, the antithrombotic drug is one or more of an anticoagulant drug and an antiplatelet drug. In one embodiment, the anticoagulant drug is selected from the group consisting of heparin or a pharmaceutically acceptable salt thereof, low-molecular-weight heparin or a pharmaceutically acceptable salt thereof, and recombinant hirudin. In one embodiment, the antiplatelet drug is selected from the group consisting of aspirin, clopidogrel and ticlopidine.

In one embodiment, the primary hemorrhagic transformation is spontaneous hemorrhagic transformation after acute cerebral infarction.

In one embodiment, in the bleeding complication of a thrombolytic or antithrombotic drug for myocardial infarction, the thrombolytic drug is selected from the group consisting of urokinase, streptokinase, reteplase, alteplase, tenecteplase and lanoteplase; the antithrombotic drug is used for antithrombotic treatment in an onset stage, and primary and secondary prevention stages of myocardial infarction; and the antithrombotic drug is one or more of an anticoagulant drug or an antiplatelet drug.

In one embodiment, the antiplatelet drug is selected from the group consisting of aspirin, clopidogrel and ticlopidine; and the anticoagulant drug is selected from the group consisting of heparin or a pharmaceutically acceptable salt thereof, low-molecular-weight heparin or a pharmaceutically acceptable salt thereof, and recombinant hirudin.

In one embodiment, the bleeding complication is one or more of subcutaneous bleeding, intracranial bleeding, upper gastrointestinal bleeding or gingival bleeding.

In one embodiment, in the gastrointestinal bleeding caused by a thrombolytic or antithrombotic drug for cerebral infarction, the thrombolytic drug is one or more of urokinase, streptokinase, reteplase, alteplase, tenecteplase or lanoteplase; and the antithrombotic drug is one or more of an anticoagulant drug or an antiplatelet drug.

In one embodiment, the platelet dysfunction is platelet activation or aggregation dysfunction; and the platelet dysfunction is congenital platelet defect or acquired platelet defect.

In one embodiment, the congenital platelet defect is hereditary giant platelet syndrome, Hereditary thrombasthenia or congenital connective tissue disease; and the acquired platelet defect is caused by a drug or a disease.

In one embodiment, the drug is one or more of an antimicrobial drug, an anti-tumor drug or heparin, and the disease is one or more of uremia, diabetes, nephrotic syndrome, coronary heart disease or leukemia.

In one embodiment, the bleeding disorder caused by coagulation abnormalities is hemophilia.

In one embodiment, the hemophilia is hemophilia caused by genetic factors or secondary hemophilia; and the secondary hemophilia is caused by a drug or a autoimmune disease.

In one embodiment, the autoimmune includes but is not limited to hepatopathy, hemolysis, acquired immunodeficiency syndrome, Evans syndrome, chronic lymphocytic leukemia, various acute leukemias, lymphoma, systemic lupus erythematosus, rheumatoid arthritis inflammation or hyperthyroidism; the hepatopathy is caused by any one of chronic persistent hepatitis and liver cirrhosis; and the drug includes but is not limited to an alkylating agent, an antimetabolite, and a cytotoxic preparation chlorothiazide drug and a synergist thereof.

In one embodiment, the hemophilia is any one of hemophilia A, hemophilia B or hemophilia C.

In one embodiment, the bleeding disorder caused by anticoagulation and fibrinolysis abnormalities is an acquired disease caused by factors including but not limited to overuse of heparin or a pharmaceutically acceptable salt thereof, coumarin overdose, increased immune-related anticoagulants or overdose of thrombolytic drugs.

In efficacy example 1, a study result of an effect of icaritin on a platelet activation function shows that after 3 days of icaritin administration and peripheral anticoagulated blood of animals is activated by adenosine diphosphate (ADP) under the same condition, in all platelets labeled by CD61, an expression of CD62p is obviously increased, namely, an activation rate of platelets activated by the ADP is increased and significantly different compared with a base value before administration. It is suggested that under the experimental conditions, an intragastric administration of the icaritin can obviously promote platelet activation induced by ADP in the peripheral anticoagulated blood of rats.

A study result of an effect of the icaritin on platelet aggregation function in vitro shows that each concentration of the icaritin has an effect on promoting platelet aggregation activity induced by the ADP and the promoting effect is enhanced with an increase of the concentration, which indicates that the promoting effect of the icaritin on the platelet aggregation activity induced by the ADP is dose-dependent.

In efficacy example 2, a test of an effect of icaritin on hemorrhagic transformation after cerebral ischemia reperfusion caused by aspirin or clopidogrel indicates that the icaritin can significantly inhibit the hemorrhagic transformation after the cerebral ischemia reperfusion caused by the aspirin or clopidogrel.

In efficacy example 3, a result of an effect of icaritin on bleeding time of mice caused by heparin sodium indicates that the icaritin can significantly shorten the bleeding time of mice caused by the heparin sodium and does not affect indicators of blood routine examination and four coagulation indicators while exerting a procoagulant effect.

In efficacy example 4, a result of an effect of icaritin on bleeding time of mice caused by aspirin indicates that the icaritin can significantly shorten the bleeding time of mice caused by the aspirin.

Results of an effect of icaritin on a thrombolytic effect of a thrombolytic drug in efficacy example 5 and an effect of icaritin on hemorrhagic transformation caused by a thrombolytic drug in the efficacy example 6 results indicate that the icaritin can obviously relieve the hemorrhagic transformation caused by the thrombolytic drug, does not affect a thrombolytic effect on thrombi by the thrombolytic drug while preventing the hemorrhagic transformation and reducing hemorrhage volume, and does not affect indicators of blood routine examination. The icaritin also has a remarkable effect on preventing and treating hemorrhagic transformation caused by thrombolytic drugs, anticoagulant drugs and antiplatelet drugs other than those listed in the above examples, and also has a remarkable effect on reducing risks of spontaneous hemorrhagic transformation and asymptomatic hemorrhagic transformation. In addition to having a remarkable effect on preventing and treating hemorrhagic transformation after cerebral infarction, the icaritin also has a remarkable effect on preventing and treating occurrence of hemorrhagic infarction which can be determined according to skull CT/MRI for the first time.

Test results of a preventive effect of icaritin on gastrointestinal bleeding caused by aspirin in efficacy example 7 and a preventive effect of icaritin on gastric bleeding caused by a thrombolytic drug in efficacy example 8 indicate that the icaritin can reduce an incidence rate of gastrointestinal bleeding caused by a thrombolytic drug, high-dose icaritin has a significant preventive effect on gastrointestinal bleeding caused by a thrombotic disease itself, and the effects are both dose-dependent.

In efficacy example 9, an experimental result of icaritin on bleeding complications caused by a thrombolytic drug indicates that the icaritin can significantly reduce an incidence of the bleeding complications of myocardial infarction caused by a thrombolytic drug and does not affect a thrombolytic effect of the thrombolytic drug when used in combination with the thrombolytic drug.

In efficacy example 10, a result of an effect of icaritin on bleeding time of coagulation factor IX-knockout mice with hemophilia indicates that the icaritin can effectively shorten the bleeding time of IX knockout mice and results of blood routine examination show no significant difference among mice of each group.

In efficacy example 11, a result of an effect of icaritin on activated partial thromboplastin time of acquired hemophilia A indicates that the icaritin can significantly shorten the activated partial thromboplastin time of patients with hemophilia and promote blood coagulation of the patients.

The icaritin has a significant therapeutic effect on hemophilia caused by genetic factors as well as secondary hemophilia.

When the icaritin is used for preventing and treating bleeding disorders, an administration route comprises an enteral route and a parenteral route, and the parenteral route includes but is not limited to subcutaneous, intradermal, arterial, intravenous, intramuscular, articular, intrathecal, intracranial, thoracic, intraperitoneal injection or instillation, nasal, buccal, sublingual, tracheal, urethral, rectal or lesion local administration and the like. The icaritin can be taken simultaneously with other drugs or in advance for preventive administration.

The present disclosure provides use of icaritin in preparing a drug for preventing and treating bleeding disorders and also provides a pharmaceutical formulation for treating the above diseases. The pharmaceutical formulation comprises the icaritin and a pharmaceutically acceptable pharmaceutical excipient.

The pharmaceutical excipient used in the formulation of the present disclosure is common and known to a person skilled in the art.

Suitable pharmaceutical excipients are described in detail in the "pharmaceutical excipients" (compiled by Luo Mingsheng and Gao Tianhui, published by Sichuan Science and Technology Press, 1993, Page 123). For example, common pharmaceutical excipients for preparing a microemulsion formulation include but are not limited to soybean oil, polyoxyethylene-23-lauryl ether, 1,2-propylene glycol, hydrogenated coco-glycerides, lauroyl macrogol-32-glyceride, polyethylene glycol 3350, safflower seed oil, cottonseed oil, and decaglycerol monostearate; common pharmaceutical excipients for preparing a dropping pill formulation include but are not limited to polyethylene glycol 6000 and polyethylene glycol 1000; and common pharmaceutical excipients for preparing a capsule formulation include but are not limited to lactose and corn starch. A pharmaceutically acceptable carrier commonly used for preparing a soft capsule formulation includes but is not limited to medium-chain fatty acid glycerides, polyoxyethylene castor oil, 1,2-propylene glycol, and the like.

A person skilled in the art can select suitable pharmaceutical excipients according to actual needs and formulate the formulation of the present disclosure by methods known in the art. The formulation includes but is not limited to a solid, a liquid, an oil, an emulsion, a gel, an aerosol, an inhalant, a spray, a capsule, a pill, a patch, a suppository, and the like.

The icaritin of the present disclosure can relieve platelet dysfunction, shorten thromboplastin time, and promote blood coagulation, and can be used for preventing and treating platelet dysfunction and bleeding disorders caused thereby, bleeding disorders caused by coagulation abnormalities, bleeding disorders caused by vessel wall abnormalities or bleeding disorders caused by anticoagulation and fibrinolysis abnormalities.

DETAILED DESCRIPTION OF THE EMBODIMENTS

The present disclosure is further described by the specific embodiments, but is not only limited to the following examples.

Formulation Example 1 Icaritin Microemulsion Formulation

| Icaritin | 10 g | Soybean oil | 35 g |
|---|---|---|---|
| Polyoxyethylene-23-lauryl ether | 60 g | 1,2-propylene glycol | 30 g |

Preparation process: soybean oil, polyoxyethylene-23-lauryl ether and 1,2-propylene glycol were weighed according to the prescription amount, the materials were mixed and uniformly stirred, icaritin was added to be dissolved, ultrasonic treatment can be performed to accelerate the dissolution, and a clear solution, namely an icaritin microemulsion formulation, was obtained. The particle size of the icaritin microemulsion formulation was measured by a laser particle size analyzer and an average particle size was 15 nm.

Formulation Example 2 Icaritin Microemulsion Formulation

| Icaritin | 0.1 g | Hydrogenated coco-glycerides | 5 g |
|---|---|---|---|
| Lauroyl macrogol-32-glyceride | 20 g | 1,2-propylene glycol | 5 g |
| Polyethylene glycol 3350 | 20 g | | |

Preparation process: hydrogenated coco-glycerides, lauroyl macrogol-32-glyceride, 1,2-propylene glycol and polyethylene glycol 3350 were weighed according to the prescription amount, the materials were mixed and uniformly stirred, icaritin was added to be dissolved, ultrasonic treatment can be performed to accelerate the dissolution, and a clear solution, namely an icaritin microemulsion formulation, was obtained. The particle size of the icaritin microemulsion formulation was measured by a laser particle size analyzer and an average particle size was 40 nm.

Formulation Example 3 Icaritin Injection

| Icaritin | 500 g | PEG-400 | 2 L |
|---|---|---|---|
| Ethanol | 0.5 L | 0.9% sodium chloride solution | supplemented to a total of 10 L |

Preparation process: icaritin was added into PEG-400 of the prescription amount, the materials were stirred to be dissolved, 0.9% sodium chloride solution was added to 10 L, the materials were stirred uniformly, 0.5% of needle activated carbon was added, the materials were stirred and the carbon was removed to obtain a finished product.

Formulation Example 4 Icaritin Injection

| Icaritin | 10 g | Ethanol | 2 L |
| Tween-80 | 1,500 g | Water for injection | supplemented to 10 L |

Preparation process: ethanol and Tween-80 of the prescription amount were mixed uniformly, icaritin was added, the materials were stirred to be dissolved, water for injection was added to 10 L, the materials were stirred uniformly, 0.5% of needle activated carbon was added, the materials were stirred and the carbon was removed to obtain a finished product.

Formulation Example 5 Icaritin Injection

| Icaritin | 1 g | Ethanol | 3.3 L |
| Water for injection | supplemented to 10 L | | |

Preparation process: icaritin was added to ethanol of the prescription amount, the materials were stirred to be dissolved, water for injection was added to 10 L, the materials were stirred uniformly, 0.5% of needle activated carbon was added, the materials were stirred and the carbon was removed to obtain a finished product.

Formulation Example 6 Icaritin Dropping Pill Formulation

| Icaritin | 5.0 g | Polyethylene glycol 6000 | 14.5 g |
| Polyethylene glycol 1000 prepared into 1,000 pills 5.0 g | | | |

Preparation process: icaritin passing through a 100-mesh sieve of the prescription amount was weighed and added into a mixed solution heated and melted on a water bath and containing Polyethylene glycol 6000 and Polyethylene glycol 1000 of the prescription amount, the materials were fully stirred to be uniform, an obtained mixture was filled into a dropping bottle and dropped at a temperature of 95±2° C. into a glass condensing column containing 4-6 mL of methyl silicone oil to be shaped, the shaped materials were taken out, and the adhered methyl silicone oil was absorbed with absorbent paper to be removed to obtain a finished product.

Formulation Example 7 Icaritin Enteric Soft Capsule Formulation

Prescription of Contents:

| Icaritin | 10 g | Anhydrous ethanol | 10 g |
| 1,2-propylene glycol | 10 g | Polyoxyethylene castor oil | 50 g |
| Medium-chain fatty acid glycerides | 20 g | | |

Prescription of Gel Skin:

| Gelatin | 10 g | Glycerin | 5 g |
| Purified water | 10 g | | |

Prescription of Enteric Coating Solution:

| Eudragit L30D-55 | 100 g | Triethyl citrate | 3 g |
| Talcum powder | 7.5 g | Purified water | 200 g |

Preparation process: medium-chain fatty acid glycerides, polyoxyethylene castor, 1,2-propylene glycol and anhydrous ethanol were weighed according to the prescription amount, the materials were mixed and uniformly stirred, icaritin was added to be dissolved, ultrasonic treatment can be performed to accelerate the dissolution, and contents of a soft capsule microemulsion were obtained. Gelatin, glycerin, and purified water were weighed, the materials were mixed uniformly, and an obtained mixture was pressed into a gel skin. Eudragit L30D-55, triethyl citrate, talcum powder and purified water of the prescription amount were weighed, and the materials were mixed uniformly to prepare an enteric coating solution. The contents of the soft capsule microemulsion containing icaritin were wrapped with the gel skin to be prepared into a soft capsule, and an enteric coating was applied to the soft capsule to prepare an enteric soft capsule.

Formulation Example 8 Icaritin Capsule Formulation

| Icaritin | 50 g | Lactose | 120 g |
| Corn starch | 130 g | Magnesium stearate | 5 g |

Preparation process: 100 g of icaritin, 120 g of lactose and 130 g of corn starch were mixed in a mixer for 10-15 min, 5 g of magnesium stearate was added, the materials were mixed for 1-3 min, and an obtained mixture was packed into 1,000 capsule shells to obtain a finished product.

Formulation Example 9 Icaritin Tablet

| Icaritin | 50 g | Microcrystalline cellulose | 200 g |
| Sodium carboxymethyl starch | 8 g | Magnesium stearate | 1.5 g |
| 8% starch syrup | appropriate amount | | |

Preparation process: icaritin and auxiliary materials microcrystalline cellulose and sodium carboxymethyl starch were mixed uniformly, an appropriate amount of starch pulp was added to prepare a soft material, and the material passed through a 16-mesh sieve to be granulated. Wet granules were dried at 60° C., the dried granules were sieved through a 20-mesh sieve to be separated, fine powder in the dried granules was sieved out to be mixed with magnesium stearate, a mixture was mixed uniformly with the dried granules, and the materials were pressed into tablets about 260 mg each tablet.

Formulation Example 10 Icaritin Powder for Injection

| Icaritin | 10 g | Glucose | 500 g |
|---|---|---|---|
| Water for injection supplemented to 10 L prepared into a total of 2,000 freeze-dried products | | | |

Preparation process: an icaritin raw material for injection of the prescription amount was weighed and an appropriate amount of water for injection was added to dissolve. Glucose of the specified amount and pre-sterilized and depyrogenated was added to be uniformly mixed and water for injection was added to the specified 10 L; and 50 g of activated carbon for injection was added to the above medicinal solution, the solution was heated at 60-80° C. for 30 min, the heated solution was filtered with a membrane and a filtrate was collected. The filtrate was subjected to positive-pressure sterile filtration with a sterile filter according to an aseptic operation method and filtered with a 0.22 μM microporous membrane. The filtrate was inspected for pyrogen and semi-finished product content and sub-packaged into penicillin vials. In a special freeze-drying box, pre-freezing was performed at −40° C. for 1.5-3.5 h, sublimation was performed under vacuum to remove 90% of free moisture, heat drying (at a maximum temperature not exceeding 35° C.) was performed and icaritin powder for injection can be prepared after the freeze-drying.

Efficacy Example 1 Effects of Icaritin on Platelet Activation Function and Platelet Aggregation Function In Vitro 1. Effect of Icaritin on Platelet Activation Function 1.1 Experimental Animal SD rats were SPF grade and weighed 250-300 g. Half of the rats were female and the rest was male, and the female rats were not pregnant.

1.2 Detection of Platelet Activation By Flow Cytometry 0.5 mL of blood was collected from the orbit of the rat and 3.8% sodium citrate was added for anticoagulation (a ratio of blood to anticoagulant was 9:1) to prepare anticoagulated blood. 50 μL of anticoagulated blood was taken from each animal for determination of spontaneous platelet activation rate; and another 50 μL of anticoagulated blood was taken and 50 μL of adenosine diphosphate with a final concentration of 10 μmol was added for activation. 1.0-1.5 μL of each of CD62pPE/Cy7 and CD61PE was added to double-label the 2 anticoagulated blood, CD61 was used to label all the platelets and CD62p was used to label the activated platelets. 50 μL of the anticoagulated blood was taken and 50 μL of adenosine diphosphate with a final concentration of 10 μmol was added for activation. The rats were double-labeled with G2a-PE/Cy7 and G-PE by intragastrical administration as a control. Each tube containing the treated blood was incubated at 4° C. in a dark place for 20 min; and 0.5 mL of 4% paraformaldehyde was added to fix for 10 min. 50 μL of the fixed blood sample was taken and diluted with 1 mL of a diluent, and the diluted sample was analyzed on a flow cytometer. Platelet populations were delineated in a CD61PE/Side Angle Light Scattering (SSC) two-parameter scatterplot, 5,000 platelets were counted, the number of CD61 and CD62p-positive cells was further counted in a CD61/CD62p scatterplot, and a percentage of a positive expression rate of CD62p in an expression rate of CD61 reflected a platelet activation rate (%).

1.3 Effects of Icaritin on Platelet Activation Induced By Adenosine Diphosphate in Rats Twenty-four rats were taken and divided into 3 groups with 8 rats in each group. The rats were separately intragastrically administrated with 3, 6, and 18 mg/kg of icaritin once a day for 3 consecutive days. 1.0 mL of blood was collected from the orbits before administration and 20 min after a last administration, wherein 0.5 mL was used for a blood routine examination and 0.5 mL was used to prepare anticoagulated blood. The blood was treated and analyzed on the flow cytometer according to the detection method of platelet activation by flow cytometry. An activation rate of platelets activated by adenosine diphosphate (basic value) before administration and an activation rate of platelets activated by adenosine diphosphate after administration were compared. At the same time, 50 μL of anticoagulated blood was taken from the rats before administration, adenosine diphosphate was not added, and a spontaneous activation rate of the anticoagulated blood of animals was measured using the same method. The animals were fasted for 16-24 h before each blood sampling.

1.4 Test Items and Test Results (1) Effects on Platelet Activation Induced by Adenosine Diphosphate in Rats After the peripheral anticoagulated blood of the animals was activated by adenosine diphosphate before administration, a proportion of activated platelets in all platelets labeled by CD61 was significantly increased compared with a spontaneous activation rate, that is, an expression of CD62p was significantly increased, indicating that the adenosine diphosphate can induce an increased activation rate of platelets. After 3 days of icaritin administration and peripheral anticoagulated blood of animals was activated by adenosine diphosphate under the same condition, in all platelets labeled by CD61, an expression of CD62p was obviously increased, namely, an activation rate of platelets activated by the adenosine diphosphate was increased and significantly different compared with a base value before administration. It is suggested that under the experimental conditions, an intragastric administration of the icaritin can obviously promote platelet activation induced by the adenosine diphosphate in the peripheral anticoagulated blood of rats. The specific results were shown in Table 1.

TABLE 1

Comparison of activation rate of platelets activated by adenosine diphosphate before and after in-vivo administration

| Dose (mg/ kg) | Number of animals (n) | Spontaneous activation rate | Activation rate of platelets activated by adenosine diphosphate | | Activation-promoting rate (%) |
|---|---|---|---|---|---|
| | | | Basic value | After administration | |
| 3 | 8 | 0.60 ± 0.11 | 44.02 ± 11.21 | 58.16 ± 13.41 | 32.12 |
| 6 | 8 | 0.59 ± 0.20 | 47.19 ± 13.12 | 65.23 ± 16.78 | 38.22 |
| 18 | 8 | 0.61 ± 0.14 | 50.34 ± 19.22 | 78.45 ± 20.22 | 55.84 |

(2) Blood Routine Examination

There was no significant difference in indicators of blood routine examination of each-dose icaritin group before and after administration, especially the number of platelets. The results indicated that the icaritin did not affect the number of platelets while increasing activity of the platelets and were shown in Table 2.

TABLE 2

| | Effects of icaritin on blood routine examination of rats induced by adenosine diphosphate | | | |
|---|---|---|---|---|
| | Number of platelets ($10^9$/L) | Number of leukocytes ($10^9$/L) | Number of erythrocytes ($10^{12}$/L) | Concentration of hemoglobin (g/L) |
| Before administration | 1203 ± 127 | 1.759 ± 0.213 | 6.457 ± 0.675 | 154.5 ± 10.9 |
| 3 mg/kg | 1124 ± 209 | 1.832 ± 0.154 | 7.213 ± 0.554 | 180.5 ± 11.2 |
| 6 mg/kg | 1397 ± 143 | 1.653 ± 0.421 | 6.783 ± 0.871 | 179.0 ± 9.2 |
| 18 mg/kg | 1249 ± 166 | 1.761 ± 0.335 | 7.235 ± 0.656 | 181.6 ± 9.5 |

2. Effect of Icaritin on Platelet Aggregation Function In Vitro

2.1 Experimental Method of In-Vitro Promotion of Platelet Aggregation Activity After domestic rabbits were locally anesthetized with procaine, common carotid artery was surgically separated, blood was collected and anticoagulated with 3.8% sodium citrate, the anticoagulated blood was centrifuged at 800 r/min for 10 min to prepare platelet-rich plasma (PRP), the remaining part was centrifuged at 300 r/min for 10 min to prepare platelet-poor plasma (PPP), and a platelet aggregation experiment was performed. 265 μL of PRP and 30 μL of icaritin were added to a test tube (to enable final concentrations of the icaritin to be 0.1 mmol/L, 0.5 mmol/L, and 5 mmol/L separately), incubation was performed for 5 min, 5 μL of adenosine diphosphate (at a final concentration of 25 μmol/L) was added as an inducer, and a maximum aggregation rate within 5 min was observed and recorded. 1% by mass of dimethyl sulfoxide was used as a control and a promoting effect of the icaritin of each concentration on platelet aggregation induced by adenosine diphosphate was observed.

2.2 Experimental Result

A promoting effect of different concentrations of icaritin on platelet aggregation induced by adenosine diphosphate in vitro was shown in Table 3. It can be seen from the table that each concentration of the icaritin had an effect on promoting platelet aggregation activity induced by the adenosine diphosphate and the promoting effect was enhanced with an increase of the concentration, which indicated that the promoting effect of the icaritin on the platelet aggregation activity induced by the adenosine diphosphate was dose-dependent.

TABLE 3

| In-vitro promotion of icaritin on platelet aggregation activity induced by adenosine diphosphate | | |
|---|---|---|
| Groups | Concentration | Aggregation-promoting rate (%) |
| Low-dose icaritin group | 0.1 mmol/L | 23.3 ± 4.5 |
| Medium-dose icaritin group | 0.5 mmol/L | 38.9 ± 8.7 |
| High-dose icaritin group | 5 mmol/L | 52.2 ± 9.0 |

Efficacy Example 2 Effect of Icaritin on Hemorrhagic Transformation After Cerebral Ischemia Reperfusion Caused By Aspirin or Clopidogrel

1. Experimental Process

1.1 Model Establishment and Experimental Method 150 male ICR mice of SPF grade and weighed 27-30 g were purchased from Jinan Pengyue Experimental Animal Breeding Co., Ltd. Animal certificate number: No.1107262011001201 and No.1107262011001347.

The mice were quarantined for 3-7 days after entering a laboratory and healthy (female and nulliparous) mice were selected as test animals. The main inspection contents during the quarantine period included but were not limited to whether the number, quality indicators, general states and body weight of the animals were consistent with requirements in the application; and non-conformity animals were not included in the experiment.

The specific results were shown in Table 4.

TABLE 4

| | Grouping and administration of mice | | | | | |
|---|---|---|---|---|---|---|
| Groups | Number of animals | Drug | Administration dose | Administration route | Administration frequency | Administration time |
| Control group (C) | 10-12 | Sodium carboxymethylcellulose | 0.5% | Intragastric administration (i.g) | Once a day | Day 1-Day 3 |
| Model group (V) | 10-12 | Sodium carboxymethylcellulose | 0.5% | i.g | Once a day | Day 1-Day 3 |
| Icaritin-3 mg/kg (L) | 10-12 | Aspirin or clopidogrel or Icaritin | 100 mg/kg or 15 mg/kg 3 mg/kg | i.g | Once a day | Day 1-Day 3 |

TABLE 4-continued

| | | | | Grouping and administration of mice | | |
|---|---|---|---|---|---|---|
| Groups | Number of animals | Drug | Administration dose | Administration route | Administration frequency | Administration time |
| Icaritin-6 mg/kg (L) | 10-12 | Aspirin or clopidogrel or Icaritin | 100 mg/kg or 15 mg/kg 6 mg/kg | i.g | Once a day | Day 1-Day 3 |
| Icaritin-12 mg/kg (H) | 10-12 | Aspirin or clopidogrel or Icaritin | 100 mg/kg or 15 mg/kg 12 mg/kg | i.g | Once a day | Day 1-Day 3 |
| Icariin-12 mg/kg (H) | 10-12 | Aspirin or clopidogrel or Icariin | 100 mg/kg or 15 mg/kg 12 mg/kg | i.g | Once a day | Day 1-Day 3 |

Note:
The day of start of administration is defined as Day 1.

5-week-old ICR male mice were fed to 6-week-old and divided into a control group, a model group, an icaritin-3 mg/kg group, an icaritin-6 mg/kg group, an icaritin-12 mg/kg group, and an icariin-12 mg/kg group according to body weight. From day 1 to day 3 after the grouping, the mice in each icaritin group were separately intragastrically administrated with 3, 6, and 12 mg/kg of icaritin and the mice in the icariin group was intragastrically administrated with 12 mg/kg of icariin once a day, and the mice in other groups were intragastrically administrated with a corresponding vehicle; and except the control group, the mice in other groups were intragastrically administrated with aspirin (100 mg/kg) or clopidogrel (15 mg/kg) once a day at a volume of 10 mL/kg.

On day 3, 10 min after the administration, the mice were anesthetized by intraperitoneal injection of 70 mg/kg of pentobarbital sodium and subjected to a cerebral ischemia-reperfusion (middle cerebral artery occlusion, MCAO) surgery with ischemia for 1 h and reperfusion for 23 h.

24 h after the surgery was an end point of the experiment.

1.2 Detection Indicators

Bleeding rate: the mice were anesthetized by intraperitoneal injection of 70 mg/kg of pentobarbital sodium, a brain tissue was taken out, cerebral hemorrhage was recorded and a bleeding rate of the mice in each group was calculated. Cerebral hemorrhage rate %=number of animals with cerebral hemorrhage/number of surviving animals in each group×100.

2. Data Processing

All data were input into an Excel file, subjected to a statistical analysis with SPSS 17.0, and expressed as mean±standard deviation (mean±SD). The experimental data were statistically analyzed and compared by one-way ANOVA and a t-test.

3. Experimental Results

Effect on Bleeding Rate
The experimental results showed that in a hemorrhagic transformation model induced by aspirin combined with cerebral ischemia-reperfusion, the bleeding rate of the model group was 85.7%, the bleeding rate was significantly decreased after pre-administration of icaritin for prevention, the bleeding rates of the icaritin-3 mg/kg group, the icaritin-6 mg/kg group, and the icaritin-12 mg/kg group were 37.5%, 25.0%, and 22.2% separately, and the bleeding rate was not significantly decreased after pre-administration of icariin for prevention. The results were shown in Table 5.

In a hemorrhagic transformation model induced by clopidogrel combined with cerebral ischemia-reperfusion, the bleeding rate of the model group was 80%, the bleeding rate was significantly decreased after pre-administration of icaritin for prevention, the bleeding rates of the icaritin-3 mg/kg group, the icaritin-6 mg/kg group, and the icaritin-12 mg/kg group were 42.9%, 25.0%, and 25.0% separately, and the bleeding rate was not significantly decreased after pre-administration of icariin for prevention. The results were shown in Table 6.

TABLE 5

Effect of icaritin on bleeding rate of hemorrhagic transformation after cerebral ischemia caused by aspirin

| Groups | Number of animals | Number of animals with cerebral hemorrhage | Bleeding rate % |
|---|---|---|---|
| Control group | 10 | 0 | 0 |
| Model group | 7 | 6 | 85.7 |
| Icaritin-3 mg/kg | 8 | 3 | 37.5 |
| Icaritin-6 mg/kg | 8 | 2 | 25.0 |
| Icaritin-12 mg/kg | 9 | 2 | 22.2 |
| Icariin-12 mg/kg | 8 | 6 | 75.0 |

TABLE 6

Effect of icaritin on bleeding rate of hemorrhagic transformation after cerebral ischemia caused by clopidogrel

| Groups | Number of animals | Number of animals with cerebral hemorrhage | Bleeding rate % |
|---|---|---|---|
| Control group | 10 | 0 | 0 |
| Model group | 5 | 4 | 80.0 |
| Icaritin-3 mg/kg | 7 | 3 | 42.9 |
| Icaritin-6 mg/kg | 8 | 2 | 25.0 |
| Icaritin-12 mg/kg | 8 | 2 | 25.0 |
| Icariin-12 mg/kg | 7 | 5 | 71.4 |

In the study, an antiplatelet drug (aspirin or clopidogrel) combined with cerebral ischemia-reperfusion was used to successfully establish a hemorrhagic transformation model according to references. A preventive effect of the icaritin on the hemorrhagic transformation animal model was investigated by bleeding.

In the study, a mouse model of hemorrhagic transformation was successfully replicated, the bleeding rate was significantly increased, and after icaritin was administrated for prevention, the above indicators were significantly decreased, indicating that the icaritin can significantly inhibit hemorrhagic transformation after cerebral ischemia-reperfusion caused by aspirin or clopidogrel.

Efficacy Example 3 Effect of Icaritin on Prolonged Bleeding Time in Mice Caused By Heparin Sodium 1. Drugs and Sources Heparin sodium injection (Source: Wanbang Biopharmaceuticals; Batch number: 51701106)
Etamsylate injection (Source: Shandong Fangming Pharmaceutical Group Co., Ltd.; Batch number: 18060672)

2. Test Animals and Grouping

72 ICR mice aged 5-6 weeks, weighing 19-21 g, and half male and half female were selected. The mice were quarantined for 7 days after entering a laboratory and healthy mice were selected as test animals. The mice were weighed on first and last days of quarantine. According to the body weight on the last day of the quarantine, the male and female animals were divided into six groups by a simplified random method, namely, a normal group (C), a model group (V), low-, medium- and high-dose icaritin groups (2, 6, and 18 mg/kg, L, M, H) and a positive control drug group (200 mg/kg of etamsylate, P).

3. Pre-Administration and Modeling

After the grouping, the mice in the normal group and the model group were intragastrically administrated with 10 ml/kg of an icaritin solvent which was prepared by adding 12 g of hypromellose E5 and 0.1 g of sodium lauryl sulfate into 1 L of water. The mice in each dose group of icaritin were separately intragastrically administrated with 2, 6, and 18 mg/kg of icaritin once a day for five consecutive days; and the mice in the positive control drug group were intraperitoneally injected with 200 mg/kg of an etamsylate injection once a day for five consecutive days. One hour after the last pre-administration, the mice in the model group and each administration group were injected with 150 U/kg of a heparin sodium injection through a tail vein to establish a model, and the mice in the normal group were injected with 10 ml/kg of a sodium chloride injection through a tail vein.

4. Detection Indicators 4.1 Bleeding Time

After 15 min of the modeling, the tails of the mice were cut and bleeding time of each mouse was measured.

4.2 Indicators of Blood Routine Examination and Four Coagulation Indicators

After the bleeding time was detected, the mice were anesthetized with sodium pentobarbital, blood was collected from an abdominal cardinal vein, and indicators of blood routine examination and four coagulation indicators (prothrombin time, thromboplastin time, thrombin time, and fibrinogen) were detected.

5. Test Results 5.1 Bleeding Time

The bleeding time of the mice in each group was shown in Table 7.

TABLE 7

| Effect of icaritin on bleeding time in mice caused by heparin sodium | | |
|---|---|---|
| Groups | Number of animals | Bleeding time (min) |
| C | 12 | $16.2 \pm 3.3$ |
| V | 12 | $35.5 \pm 9.8^{\#\#}$ |
| P | 12 | $21.4 \pm 6.7^{\$}$ |
| L | 12 | $26.4 \pm 8.8^{\$}$ |
| M | 12 | $22.7 \pm 9.1^{\$}$ |
| H | 12 | $15.9 \pm 6.6^{\$ \ \$ \ \&}$ |

Note:
Compared with the normal group,
$^{\#\#}$indicates $P < 0.01$; compared with the model group,
$^{\$}$indicates $P < 0.05$ and
$^{\$ \ \$}$indicates $P < 0.01$; and compared with the positive control drug group,
$^{\&}$ indicates $P < 0.05$.

It can be seen from the table that compared with the normal group, the bleeding time of the mice in the model group was significantly prolonged, indicating that the modeling was successful; compared with the model group, the bleeding time of the mice in each administration group was significantly shortened, indicating that icaritin could shorten the bleeding time of the bleeding mice; and the bleeding time was more significantly shortened with increase of the dose, indicating that a coagulation-promoting effect of the icaritin was dose-dependent, and the bleeding time was significantly different between the mice in the high-dose group and the positive control drug group, indicating that a coagulation-promoting effect of the icaritin was better than that of the positive control drug.

5.2 Indicators of Blood Routine Examination and Four Coagulation Indicators

Results of indicators of blood routine examination and four coagulation indicators of the mice in each group were separately shown in Table 8 and Table 9.

TABLE 8

| Results of indicators of blood routine examination of mice in each group | | | | |
|---|---|---|---|---|
| Groups | Number of platelets $(10^9/L)$ | Number of leukocytes $(10^9/L)$ | Number of erythrocytes $(10^{12}/L)$ | Concentration of hemoglobin $(g/L)$ |
| C | $1117 \pm 181$ | $1.989 \pm 0.213$ | $7.034 \pm 0.675$ | $132.4 \pm 9.9$ |
| V | $1056 \pm 161$ | $1.896 \pm 0.197$ | $7.135 \pm 0.554$ | $140.5 \pm 8.7$ |
| P | $1097 \pm 114$ | $1.903 \pm 0.221$ | $6.998 \pm 0.871$ | $139.0 \pm 7.2$ |
| L | $1046 \pm 136$ | $1.895 \pm 0.207$ | $7.109 \pm 0.656$ | $141.6 \pm 8.5$ |
| M | $1110 \pm 128$ | $1.934 \pm 0.199$ | $7.111 \pm 0.634$ | $153.7 \pm 9.3$ |
| H | $1059 \pm 170$ | $1.888 \pm 0.223$ | $7.090 \pm 0.761$ | $133.5 \pm 7.6$ |

TABLE 9

| | Prothrombin time (sec) | Thromboplastin time (sec) | Thrombin time (sec) | Fibrinogen (g/L) |
|---|---|---|---|---|
| Groups | | | | |
| C | 10.02 ± 1.34 | 23.23 ± 2.09 | 26.66 ± 1.34 | 1.99 ± 0.34 |
| V | 9.99 ± 1.02 | 24.12 ± 1.89 | 25.51 ± 1.78 | 1.92 ± 0.29 |
| P | 10.03 ± 1.24 | 22.78 ± 2.34 | 24.34 ± 1.37 | 1.86 ± 0.40 |
| L | 10.12 ± 1.34 | 25.19 ± 1.90 | 22.23 ± 2.01 | 1.83 ± 0.22 |
| M | 11.23 ± 1.45 | 25.09 ± 2.22 | 24.09 ± 1.99 | 1.82 ± 0.56 |
| H | 9.98 ± 1.23 | 24.55 ± 2.66 | 25.54 ± 1.78 | 2.01 ± 0.52 |

Results of four coagulation indicators of mice in each group

It can be seen from the table that there were no significant differences in the indicators of blood routine examination and the four coagulation indicators among the mice in each group, indicating that the icaritin had no significant effect on the indicators of blood routine examination and the four coagulation indicators when shortened the prolonged bleeding time caused by heparin sodium.

Efficacy Example 4 Effect of Icaritin on Prolonged Bleeding Time in Mice Caused By Aspirin 1. Drugs and Sources Aspirin (Source: Shantou Jinshi Pharmaceutical Factory Co., Ltd.; Bach. number: 1903012)

Etamsylate injection (Source: Shandong Fangming Pharmaceutical Group Co., Ltd.; Batch number: 1905032)

2. Test Animals and Grouping

96 ICR mice aged 5-6 weeks, weighing 19-21 g, and half male and half female were selected. The mice were quarantined for 7 days after entering a laboratory and healthy mice were selected as test animals. The mice were weighed on first and last days of quarantine.

According to the body weight on the last day of the quarantine, the male and female animals were divided into six groups by a simplified random method, namely, a normal group (C), a model group (V), icaritin low-, medium- and high-dose groups (2, 6, and 18 mg/kg, L, M, H) and a positive control drug group (200 mg/kg of etamsylate, P).

3. Pre-Administration and Modeling

After the grouping, the mice in the normal group and the model group were intragastrically administrated with 10 ml/kg of an icaritin solvent. The mice in each dose group of icaritin were separately intragastrically administrated with 2, 6, and 18 mg/kg of icaritin once a day for five consecutive days; and the mice in the positive drug group were intraperitoneally injected with 200 mg/kg of an etamsylate injection once a day for five consecutive days. One hour after the last pre-administration, the mice in the model group and each administration group were intragastrically administrated with 20 mg/kg of aspirin to establish a model, and the mice in the normal group were intragastrically administrated with an equal volume of normal saline.

4. Detection of Bleeding Time

After 15 min of the modeling, the tails of the mice were cut and bleeding time of each mouse was measured.

5. Test Results

The bleeding time of the mice in each group was shown in Table 10. Compared with the normal group, the bleeding time of the mice in the model group was significantly prolonged, indicating that the modeling was successful; compared with the model group, the bleeding time of the mice in each administration group was significantly shortened, indicating that icaritin could shorten the bleeding time of the bleeding mice; and the bleeding time was more significantly shortened with increase of the dose, indicating that a coagulation-promoting effect of the icaritin was dose-dependent, and the bleeding time was significantly different between the mice in the high-dose group and the positive control drug group, indicating that a coagulation-promoting effect of the icaritin was better than that of the positive control drug.

TABLE 10

| Groups | Number of animals | Bleeding time (min) |
|---|---|---|
| C | 12 | 19.2 ± 4.5 |
| V | 12 | 37.6 ± 7.8[##] |
| P | 12 | 26.4 ± 6.4[$] |
| L | 12 | 28.4 ± 9.8[$] |
| M | 12 | 24.7 ± 7.3[$] |
| H | 12 | 16.7 ± 7.2[$ $ &] |

Effect of icaritin on bleeding time in mice caused by aspirin

Note:
Compared with the normal group,
[##]indicates $P < 0.01$; compared with the model group,
[$]indicates $P < 0.05$ and
[$ $]indicates $P < 0.01$; and compared with the positive control drug group,
[&] indicates $P < 0.05$.

Efficacy Example 5 Effect of Icaritin on Thrombolytic Effect of Thrombolytic Drug 1. Construction of Rat Model of Abdominal Aortic Thrombosis A rat model of abdominal aortic thrombosis was prepared according to the following method. Rats were anesthetized by intraperitoneal injection of 40 mg/kg of 1.5% sodium pentobarbital. The abdomen fur of the rat was shaved to expose the skin and the rat was fixed on a plate in a supine position. The abdominal skin of the rat was incised, blood vessels and surrounding tissues were isolated, the abdominal aorta was exposed, and the abdominal aorta was carefully isolated with a glass needle. A 0.7 cm×1.5 cm strip of tin foil was placed under the abdominal aorta, the abdominal aorta was wrapped with a filter paper strip (0.5 cm×1.0 cm) impregnated with a 35% $FeCl_3$ solution, the filter paper strip was removed after 30 min, a color of a vascular wall was obviously darkened, thrombus formation in the blood vessel could be seen under a microscope, and a pathological section showed that the blood vessel was blocked by thrombi.

2. Grouping and Administration

The SD rats were randomly divided into 3 groups according to body weight with 10 rats in each group, namely a thrombus model group, a lumbrokinase capsule group and a lumbrokinase capsule+icaritin group. Administration was performed 5 min after the modeling, $30×10^4$ U/kg of a lumbrokinase capsule was injected directly from the duodenum, 18 mg/kg of icaritin was intragastrically administered, and the mice in the thrombus model group were intragastrically administered with an equal volume of distilled water.

3. Materials

Both ends of the abdominal aorta were clamped with hemostatic forceps, a blood vessel segment at a modeling site was completely taken, 0.5 cm of the blood vessel segment covered with a filter paper was accurately cut and weighed, and the remaining blood vessel segment was stored in 10% formaldehyde.

4. Determination of Thrombus Weight in Rats

The taken blood vessel segment was weighed with an electronic balance, the blood vessel was weighed after the thrombi were removed, and wet weight of thrombi=total weight of thrombi and blood vessels-weight of blood vessels.

The taken thrombi were dried in an oven at 80° C., placed overnight, and weighed to obtain dry weight of thrombi.

5. Test Results

The weight of thrombi in mice of each group was shown in the table below. It can be seen from the table that compared with the model group, the weight of thrombi in the lumbrokinase group was significantly decreased, indicating that a lumbrokinase had a significant thrombolytic effect; and there was no significant difference in thrombi between the lumbrokinase group and the lumbrokinase+icaritin group, indicating that icaritin did not affect a thrombolytic effect of the lumbrokinase on rat thrombi.

TABLE 11

| Effects of icaritin on weight of thrombi of rats in each group | | | |
|---|---|---|---|
| Groups | Number of cases | Wet weight of thrombi (mg) | Dry weight of thrombi (mg) |
| Model group | 9 | 2.98 ± 0.54 | 0.31 ± 0.12 |
| Lumbrokinase group | 10 | 1.01 ± 0.22[##] | 0.04 ± 0.01[##] |
| Lumbrokinase + icaritin group | 10 | 1.24 ± 0.19 | 0.04 ± 0.02 |

Note:
compared with the model group,
[##]indicates $P < 0.01$.

Efficacy Example 6 Effect of Icaritin on Hemorrhagic Transformation Induced By Thrombolytic Drug

1. Preparation of Animal Model

A rat model of middle cerebral artery autologous thrombosis was prepared according to the following method: rats were anesthetized by intraperitoneal injection of 10% chloric acid hydrate at 350 mg/kg body weight and fixed on an operating table in a supine position, skin of the rats was routinely disinfected according to aseptic operation procedures, and draping was performed. An incision about 3.0-cm-long was taken from the skin in the middle of the neck, the muscle and the subcutaneous tissue were bluntly separated, the right bilateral common carotid arteries, external carotid arteries, and internal carotid arteries were separated to avoid damage to the vagus nerve, the internal carotid arteries were separated to the skull base, and the external carotid arteries were ligated at the bifurcation of the bilateral common carotid arteries. 0.1 ml of arterial blood from the femoral artery of the rat was taken using a 1-ml syringe, 4 U of thrombin was added, the materials were uniformly mixed and stood for 8-10 min, when the blood was coagulated, and the coagulated blood was injected into a 24 G venous indwelling needle to prepare a thrombus about 1-cm-long followed by a syringe containing 1-2 ml of normal saline. The indwelling needle was punctured into the bilateral common carotid arteries in front of the bifurcation of the external carotid arteries and the internal carotid arteries and entered the internal carotid arteries anteromedially about 8-10 mm, a needle core was pulled out, the thrombus and normal saline in the syringe were rapidly injected into the internal carotid arteries, and the rats were ligated and sutured. The mice in a sham group as a control group were subjected to the same operation steps as those of thrombolysis model groups except that normal saline was injected instead of the thrombus.

2. Animal Inclusion Criteria

Symptoms and signs of the rats were observed 2 h after the modeling. The following symptoms and signs indicated that the model was successfully established: Homer's syndrome on the ipsilateral side of ischemia and turning around to the opposite side of the ischemia when walking; toppling and falling to the opposite side; and when the rats were suspended by lifting the tail, the forelimb on the opposite side of cerebral ischemia was flexed and raised, shoulder was adducted, elbow was straightened, etc.

3. Experimental Grouping and Administration 102 rats were randomly divided into a sham group, a rt-PA thrombolysis group (thrombolysis group), and rt-PA thrombolytic drug+icaritin low, medium and high-dose groups, with 18 rats in the sham group and 21 rats in each of the other groups. The rats in each group were equally divided according to different time points (3, 6, and 24 h after thrombolysis). There were 6 rats in each time point in the sham group, and 9 rats in each of the other groups at 3 h and 6 rats in each of the other groups at other time points. Another 20 rats were taken as spares and if the model failed (death or score 0), they were randomly replaced.

Except the rats in the sham group, the rats in the other groups were all administrated with alteplase (rt-PA) (5 mg/kg, sterile water for preparing the rt-PA was added to 1 ml) via the femoral vein 3 h after the modeling. The rats in the sham group were given an equal volume of normal saline.

The mice in the treatment groups were intragastrically administered with a drug twice immediately after the modeling and the thrombolytic treatment at doses of 2, 6, and 18 mg/kg separately. The rats in the sham group were given an equal volume of normal saline.

4. Indicator Observation and Determination

4.1 Overall Condition Comparison and Blood Routine Examination

4.1.1 The Overall Conditions of the Rats in the Sham Group, the Thrombolysis Group and the Thrombolytic Drug+Each-Dose Icaritin Group were Compared

4.1.2 Blood Routine Examination of the Rats in the Sham Group, the Thrombolysis Group and the Thrombolytic Drug+Each-Dose Icaritin Group was Performed

4.2 Determination of Cerebral Infarction Volume (Rate)

Except the mice in the sham group, 3 rats in each group were sacrificed at 3 h after the thrombolysis, the brain tissue was quick-frozen in a −20° C. refrigerator for 20 min and prepared into 2-mm thick coronal brain slices, the slices were immersed in a 2% thrombin solution, subjected to water bath at 37° C. in a dark place for 30 min, and placed in a 4% paraformaldehyde solution to be fixed for 24 h, the fixed slices were photographed the infarct volume was determined using an image analysis software (Image-ProPlus 6.0). Infarct volume=non-ischemic side hemisphere volume-ischemic side hemisphere non-infarct area volume, and an infarct volume ratio was expressed as the percentage (%) of the infarct volume to the non-ischemic side hemisphere volume.

4.3 Determination of Cerebral Hemorrhage Volume

(1) Drawing of Standard Curve

Another 4 healthy rats were taken, sacrificed by excessive anesthesia, and subjected to cardiac perfusion. Blood was taken. Eight cerebral hemisphere tissues were taken, 0, 0.5, 1, 2, 4, 8, 16, 32, and 50 μL of arterial blood of male SD rats was successively added to each hemisphere tissue, PBS at a pH of 7.4 was added to a total volume of 3 ml, the tissue was homogenized for 30 s and ultrasonically lysed, and centrifugation was performed at 13,000 r/min and 4° C. for 30 min 0.8 mL of Drabkin's reagent was mixed with 0.2 mL of a supernatant of each sample, an obtained mixture was placed in a dark place at a room temperature for 10 min, and an absorbance at a wavelength of 540 nm (absorbance of sample not containing blood was set to 0) was measured. The absorbance was set as a Y-axis and the blood volume in each sample was set as an X-axis to draw a standard curve.

(2) Determination of Hemorrhage Volume in Infarct Side Hemisphere

PBS at a pH of 7.4 was added into the infarct size hemisphere tissue of the rats with cerebral infarction to a total volume of 3 ml, the tissue was homogenized for 30 s and ultrasonically lysed, and centrifugation was performed at 13,000 r/min for 30 min 0.8 mL of Drabkin's reagent was mixed with 0.2 mL of a supernatant of each sample, an obtained mixture was placed in a dark place at a room temperature for 10 min, and an absorbance at a wavelength of 540 nm (absorbance of brain tissue sample not containing blood was set to 0 and the sample of the same batch was determined) was measured. The blood volume corresponding to the obtained absorbance on the standard curve was the hemorrhage volume.

5. Statistical Analysis

All experimental data were expressed as mean±standard deviation and processed with a PASW Statistics 17.0 statistical software package. One-way analysis of variance was used for comparison between and within groups. An LSD test was performed if the variance was equal and a Dunne thrombin time T3 nonparametric test was performed if the variance was unequal. A correlation analysis was performed using a linear correlation two-tailed Pearson product-moment correlation coefficient test and a two-sided P value<0.05 was considered statistically significant.

6. Experimental Results

6.1 Overall Condition Comparison and Blood Routine Examination

6.1.1 Overall Condition Comparison

The rats in the sham group were in a good mental state and the fur color and luster were normal. Compared with the mice before operation, the mice had a significantly worse postoperative mental state in the thrombolysis group and the thrombolytic drug+each-dose icaritin group, which was manifested as dull fur color and luster, decreased spontaneous activity, and relatively sluggish response to the outside. The mice had the worst mental state in the thrombolysis group and the best mental state in the thrombolytic drug+high-dose icaritin group.

6.1.2 Blood Routine Examination

The results of blood routine examination showed that there was no significant difference in indicators of blood routine examination among the thrombolysis group and the thrombolytic drug+icaritin groups, and there was no significant difference in indicators of blood routine examination among the thrombolysis group, the thrombolytic drug+icaritin groups and the sham group.

6.2 Determination of Cerebral Infarction Volume (Rate)

A range of cerebral ischemia can be observed by thrombin time C staining Staining results: the non-infarct side brain tissue in the sham group and other groups was uniformly red, while the infarcted brain tissue was obviously edematous, pale white, and dull, and the infarcted area was white pale after the thrombin time C staining. The study results showed that the cerebral infarction volume rate was determined to be (38.84±3.67) % 3 h after the spare rats were taken to establish a model, and the thrombin time C staining of the brain tissue of the rats in the sham group had no change. Compared with the model group, the pale white area of the infarcted area was significantly decreased in the thrombolysis group and the thrombolytic drug+each-dose icaritin group by the thrombin time C staining of the rats. The determination of the cerebral infarction volume showed that a decreased rate of the cerebral infarction volume in the thrombolytic drug+each-dose icaritin group was similar to that in the thrombolysis group. The results showed that icaritin did not affect the thrombolytic effect of the thrombolytic drug.

6.3 Comparison of Cerebral Hemorrhage Volume of Rats in Each Group at Different Time Points The cerebral hemorrhage volume of the rats in each group at different time points was shown in the following table. It can be seen from the table that the hemorrhage volume in the thrombolysis group was significantly more than that in the sham group, indicating that the thrombolytic drug caused a hemorrhagic transformation of the rats with cerebral infarction and the hemorrhage volume increased with extension of time; and the hemorrhage volume in the thrombolytic drug+each-dose icaritin group was significantly decreased compared with the thrombolysis group and the hemorrhage volume did not increase with extension of time It showed that the icaritin can effectively prevent the hemorrhagic transformation caused by the thrombolytic drug.

TABLE 12

| Grouping | Number of cases | 3 h | 6 h | 24 h |
|---|---|---|---|---|
| | | Comparison of cerebral hemorrhage volume of rats in each group at different time points | | |
| Sham group | 6 | $0.04 \pm 0.02$ | $0.04 \pm 0.02$ | $0.04 \pm 0.02$ |
| Thrombolysis group | 6 | $6.43 \pm 0.89^{\#\#}$ | $9.78 \pm 1.01^{\#\#}$ | $15.32 \pm 2.01^{\#\#}$ |
| Thrombolytic drug + low-dose icaritin group | 6 | $3.09 \pm 0.78^{\$}$ | $3.34 \pm 0.99^{\$\ \$}$ | $4.22 \pm 1.66^{\$\ \$}$ |
| Thrombolytic drug + medium-dose icaritin group | 6 | $2.22 \pm 0.7^{\$\ \$}$ | $3.09 \pm 1.15^{\$\ \$}$ | $2.98 \pm 2.34^{\$\ \$}$ |
| Thrombolytic drug + high-dose icaritin group | 6 | $1.01 \pm 0.54^{\$\ \$}$ | $1.02 \pm 0.11^{\$\ \$}$ | $0.97 \pm 0.56^{\$\ \$}$ |

Note:
Compared with the sham group,
$^{\#\ \#}$indicates $P < 0.01$; and compared with the thrombolysis group,
$^{\$}$indicates $P < 0.05$ and
$^{\$\ \$}$indicates $P < 0.01$.

Efficacy Example 7 Preventive Effect of Icaritin on Gastrointestinal Bleeding Caused By Aspirin

1. Modeling and Grouping

24 SD rats were intragastrically administrated with 500 mg/kg of aspirin to establish a model of gastrointestinal bleeding, another 12 SD rats were intragastrically administrated with an equal volume of normal saline as a normal control, the rats in the bleeding model were randomly divided into a model group and an icaritin group, the mice in the icaritin group were intragastrically administrated with 18 mg/kg of icaritin during the model establishment, and the mice in the model group were intragastrically administrated with an equal volume of normal saline.

2. Dissection and Observation of Bleeding Caused By Gastric Ulcers

After 24 h of the intragastric administration, the rats were anesthetized, sacrificed, and dissected. Bleeding, erosion and ulcers of the gastric mucosa surface of the rats were observed.

3. Test Results and Discussion

The occurrence of gastric mucosal bleeding of the rats in each group was shown in Table 13. It can be seen from the table that no bleeding occurred in the normal control group and the incidence of bleeding in the model group was 66.7%; and the gastric mucosal bleeding was significantly milder and the incidence of the bleeding was significantly lower of the rats in the icaritin group than those of the rats in the model group (P<0.01), indicating that the icaritin could significantly reduce the incidence of the gastrointestinal bleeding caused by aspirin.

TABLE 13

| Groups | Comparison of gastric mucosal bleeding of rats in each group | | |
|---|---|---|---|
| | Number of animals (n) | Number of bleeding animals (n) | Bleeding rate (%) |
| Normal control group | 12 | 0 | — |
| Model group | 12 | 8 | 66.7 |
| Icaritin group | 12 | 2 | $16.7^{\#\#}$ |

Note:
compared with the model group,
$^{\#\#}$indicates $P < 0.01$.

Efficacy Example 8 Preventive Effect of Icaritin on Gastric Bleeding Caused By Thrombolytic Drug

1. Modeling and Grouping

120 SD rats were randomly divided into a sham group, a model group, a urokinase group, a high-dose icaritin+urokinase group, a medium-dose icaritin+urokinase group, and a low-dose icaritin+urokinase group, with 20 rats in each group; the rats in each-dose icaritin group were intragastrically administrated with icaritin at doses of 2 mg/kg, 6 mg/kg, and 18 mg/kg separately 4 days before operation, and the rats in the sham group, the model group and the urokinase group were intragastrically administrated with an equal volume of normal saline; and except the sham group and the model group, the rats in other groups were administered with urokinase at a dose of 5,000 u/kg, a concentration of 200 u/μL, and a volume of 20 μL by a catheter via a regional artery; and the rats in the sham group and the model group were administered with an equal volume of normal saline via a regional artery. An animal model of thrombo-embolic cerebral ischemia was prepared by blocking a middle cerebral artery with an autologous thrombus combined with a suture occlusion method, and a catheter was indwelled.

2. Indicator Observation and Determination Method

2.1 Calculation of Bleeding Rate 24 h after the arterial administration, the rats in each group were anesthetized and dissected. The number of bleeding cases was observed under naked eyes and a light microscope, and a ratio of the number of bleeding cases to the total number was calculated.

2.2 Pathological Observation of Gastric Tissue

The left lung and gastric antrum were excised, fixed with 100 g/L of a neutral formaldehyde solution, and dehydrated conventionally to be transparent, the dehydrated tissue was dipped with wax and embedded, the embedded tissue was sectioned and stained, and pathological changes were observed under a light microscope. A damage degree was graded according to a degree of tissue congestion, edema and cell degeneration from mild to severe: grade I: 0%-25%, grade II: 26%-50%, grade III: 51%-75%, and grade IV: >75% (bleeding was observed under the microscope).

3. Experiment Results and Discussion

3.1 Comparison of Bleeding Rate

Comparison of gastric bleeding rates of the rats in each group was shown in Table 14. It can be seen from the table that gastric bleeding occurred in the model group compared with the sham group, indicating that cerebral ischemia can cause gastric bleeding complications to a certain extent; the bleeding rate was significantly increased in the urokinase group compared with the model group (P<0.01), indicating that the thrombolytic drug can cause gastrointestinal bleeding complications during a thrombolytic treatment for thrombotic diseases; and the bleeding rate was significantly decreased in each-dose icaritin+urokinase group compared with the urokinase group (all P<0.01), indicating that icaritin had an effect of reducing the gastrointestinal bleeding caused by the thrombolytic drug and the effect was dose-dependent.

The bleeding rate was significant different in the high-dose icaritin group compared with the model group (P<0.01), indicating that icaritin also has a certain preventive effect on gastrointestinal bleeding caused by the thrombotic diseases.

TABLE 14

Comparison of gastric bleeding rate of rats in each group

| Groups | Total number of animals (n) | Number of bleeding animals (n) | Bleeding rate (%) |
|---|---|---|---|
| Sham group | 19 | 0 | — |
| Model group | 18 | 4 | 22.2 |
| Urokinase group | 16 | 11 | 68.8$^{\$\,\$}$ |
| Low-dose icaritin + urokinase group | 17 | 5 | 29.4$^{\#\#}$ |
| Medium-dose icaritin + urokinase group | 18 | 3 | 16.7$^{\#\#}$ |
| High-dose icaritin + urokinase group | 18 | 2 | 11.1$^{\#\#\,\&}$ |

Note:
Compared with the sham group,
$^{\$\,\$}$indicates P < 0.01; compared with the urokinase group,
$^{\#\#}$indicates P < 0.01; and compared with the model group,
$^{\&}$ indicates P < 0.05.

3.2 Pathological Observation of Gastric Tissue

The pathological observation results of the gastric tissue of the rats in each group were shown in Table 15. It can be seen from the table that an incidence of gastric injury was significantly increased in the urokinase group compared with the model group (P<0.01), indicating that the thrombolytic drug can cause congestion, edema, cell degeneration, even bleeding, and other complications of the gastric tissue during the thrombolytic treatment for the thrombotic diseases; the incidence of the complications was significantly decreased in each-dose icaritin+urokinase group compared with the urokinase group (P<0.01 or P<0.05), indicating that the icaritin can reduce the complications of congestion, edema, cell degeneration and even bleeding of the gastrointestinal tissue caused by the thrombolytic drug. Besides, the incidence of the complications was significantly decreased in the high-dose icaritin+urokinase group compared with the urokinase group. The above results indicated that the icaritin can reduce the incidence of the gastrointestinal bleeding caused by the thrombolytic drug, can also relieve symptoms of congestion, edema and cell degeneration of digestive tract tissue, and had a good recovery effect on digestive tract injury.

In addition, the results obtained from a comparison with the model group showed that the icaritin also had certain preventive and therapeutic effects on the digestive tract injury caused by ischemic diseases.

TABLE 15

Comparison of pathological grading results of gastric tissue of rats in each group

| Groups | Total number of experimental animals (n) | Number of animals (n) | | | | Total number of animals with gastric injury (n) | Incidence of gastric injury (%) |
|---|---|---|---|---|---|---|---|
| | | I | II | III | IV | | |
| Sham group | 19 | 2 | 0 | 0 | 0 | 2 | 10.5 |
| Model group | 18 | 3 | 3 | 2 | 4 | 12 | 66.7 |
| Urokinase group | 16 | 1 | 2 | 2 | 11 | 16 | 100 $^{\$\,\$}$ |
| Low-dose icaritin + urokinase group | 17 | 3 | 3 | 5 | 1 | 12 | 70.6$^{\#}$ |
| Medium-dose icaritin + urokinase group | 18 | 4 | 3 | 1 | 3 | 11 | 61.1 $^{\#}$ |
| High-dose icaritin + urokinase group | 18 | 2 | 1 | 2 | 2 | 6 | 33.3 $^{\#\,\#\,\&}$ |

Note:
Compared with the sham group,
$^{\$\,\$}$ indicates P < 0.01;
compared with the urokinase group,
$^{\#\,\#}$ indicates P < 0.01;
and compared with the model group,
$^{\&}$ indicates P < 0.05.

Efficacy Example 9 Effect of Icaritin on Bleeding Complications Caused By Thrombolytic Drug

1. Preparation of Model

60 Wistar male rats (SPF grade), weighing 220-260 g, were randomly divided into a myocardial infarction modeling group and a control group according to a random number table, with 12 rats in the control group and 48 rats in the model group. The rats were conventionally fed in separate cages with 4 rats per cage. After a normal electrocardiogram was traced, the rats in the myocardial infarction modeling group were subcutaneously injected with 150 mg·kg$^{-1}$·d$^{-1}$ of isoproterenol (ISO) in a volume of 0.2 mL/100 g every other 24 h for 2 consecutive days. The rats in the control group were subcutaneously injected with a same amount (0.2 mL/100 g) of normal saline according the same method for 2 consecutive days. The electrocardiogram was monitored 24 h after the second subcutaneous injection of the isoproterenol. After the rats were anesthetized with ether, the six-lead (extremity lead) electrocardiogram of the rats was recorded before and after the injection, the heart rate was measured and shifting degrees of Q wave and ST segment were observed to evaluate whether the model was successful. The ST segment elevation of greater than 0.2 mV in lead II or the formation of Q wave became the standard for myocardial infarction.

2. Grouping and Administration

A total of 36 modeled rats were selected from the modeling group and randomly divided into a model group, a thrombolysis group and a thrombolytic drug+icaritin group according to the random number table. The rats in the thrombolysis group was administrated with 5 mg/kg of rt-PA via the femoral vein, the rats in the thrombolytic drug+ icaritin group was intragastrically administrated with icaritin (18 mg/kg) in addition to administration with a same dose of the thrombolytic drug, and the rats in the model group were administrated with a normal volume of normal saline via the femoral vein.

3. Detection Indicators

3.1 Electrocardiogram Monitoring of Rats in Each Group

The rats were anesthetized by inhalation of ether. After the rats entered an anesthetized state, the breathing was stable, the righting reflex disappeared, and the pain disappeared. The rat was fixed on a test bench in a supine position. Needle electrodes were subcutaneously inserted into the limbs of the rat (be careful to avoid inserting into the muscle). The electrocardiogram of the rat was monitored using the limb leads according to right upper limb-red, left upper limb-yellow, left lower limb-green, and right lower limb-black, an electrocardiograph was turned on at a paper speed of 50 mm/s and a voltage of 1 mv, and the animals were returned to the cages after the electrocardiogram.

3.2 Morphological Observation of Heart Tissue of Rats in Rach Group

After the last administration, the animal was sacrificed and fixed on a rat plate in a supine position, the skin was sterilized with 75% alcohol, the chest was quickly opened, the skin and subcutaneous tissue were cut along the midline of the sternum with tissue scissors, the left rib of the sternum and the large blood vessels were cut, the heart was taken out, residual blood in the cardiac cavity was washed away with 0.9% sodium chloride solution at 4° C., the left and right atrial appendages and the residual great blood vessels were cut off, the treated heart was dried with filter paper and weighed with an electronic scale, body weight and heart weight of the rat were calculated, the actual weight of the heart (wet weight) was weighed, and a ratio of the heart weight to the body weight (HWI=heart weight/body weight) was calculated.

3.3 Observation of Bleeding Complications of Rats in Each Group

The bleeding of the rats in each group was observed, including subcutaneous bleeding sites. After dissection, visceral bleeding and intracranial bleeding were observed.

4. Test Results and Discussion

4.1 Electrocardiogram of Each Group

Compared with the control group, the rats in the model group showed pathological Q waves, indicating that the modeling was successful; and compared with the model group, the pathological Q waves in the thrombolysis group and the thrombolytic drug+icaritin group disappeared, indicating that the thrombolytic drug can significantly relieve a myocardial infarction state in the rats with myocardial infarction and icaritin did not affect a thrombolytic effect of the thrombolytic drug.

4.2 Comparison of General Morphology of Heart of Rats in Each Group

The general morphology of the heart of the rats in each group was observed with the naked eye. Compared with the control group, the heart volume of the rats in the model group was significantly increased, the left ventricular cavity was significantly enlarged, the transmural myocardial necrosis was shown in the infarction area, and the heart was pale white and thin. The heart volume increase and transmural myocardial necrosis degree were significantly lower in the thrombolysis group and the thrombolytic drug+icaritin group than the model group. The ratio of the heart weight to the body weight of the rats in each group was shown in the table below. It can be seen from the table that there was a significant difference in the ratio of the heart weight to the body weight between the model group and the control group (P<0.01), indicating that the modeling was successful; the ratio in the thrombolysis group and the thrombolytic drug+ icaritin group was separately significantly different from the model group (both P<0.01), and there was no significant difference in the ratio between the thrombolysis group and the thrombolytic drug+icaritin group, indicating that the thrombolytic drug can significantly relieve the myocardial infarction in the rats with myocardial infarction and the icaritin did not affect the effect of the thrombolytic drug.

TABLE 16

Comparison of general morphology of heart of rats in each group

| Groups | Number of animals (n) | Body weight (g) | Whole heart weight (mg) | Heart weight/ body weight (mg/g) |
|---|---|---|---|---|
| Control group | 12 | 243.1 ± 7.9 | 634.2 ± 11.7 | 2.6 |
| Model group | 12 | 239.6 ± 8.0 | 967.7 ± 19.5 | 4.0## |
| Thrombolysis group | 12 | 246.7 ± 7.8 | 702.3 ± 10.8 | 2.8$ $ |
| Thrombolytic drug + icaritin group | 12 | 245.2 ± 4.2 | 698.9 ± 18.0 | 2.9$ $ |

Compared with the control group,
indicates $P < 0.01$; and compared with the model group,
$ $indicates $P < 0.01$.

4.3 Comparison of Bleeding Complications of Rats in Administration Groups

TABLE 17

Comparison of bleeding complications of rats in administration groups

| Groups | Total number of animals (n) | Subcutaneous bleeding (n) | Visceral bleeding (n) | Intracranial bleeding (n) | Bleeding percentage (%) |
|---|---|---|---|---|---|
| Thrombolysis group | 12 | 2 | 5 | 1 | 66.7 |
| Thrombolytic drug + icaritin group | 12 | 0 | 2 | 0 | 16.7## |

Compared with the thrombolysis group,
indicates $P < 0.01$.

It can be seen from the above table that the bleeding percentage of the thrombolytic group was significantly higher than that of the thrombolytic drug+icaritin group ($P<0.01$), indicating that the icaritin can obviously reduce the incidence of the bleeding complications caused by the thrombolytic drug.

Efficacy Example 10 Effect of Icaritin on Bleeding Time of Coagulation Factor IX-Knockout Mice with Hemophilia

1. Test Animals

IX-knockout mice with hemophilia were provided by Biocytogen Pharmaceuticals (Beijing) Co., Ltd.

2. Animal Grouping and Administration

40 IX-deficient mice with hemophilia were randomly divided into four groups, 10 mice in each group. The mice in a low-, medium-, and high-dose icaritin groups (B, C, and D) were separately intragastrically administrated with 3 mg/kg, 6 mg/kg and 18 mg/kg of icaritin once a day for 11 consecutive days. The mice in a control group (A) were intragastrically administrated with an equal volume of normal saline.

3. Detection Indicators

3.1 Determination of Bleeding Time

One hour after the last administration, the tails of the mice were cut and bleeding time of each mouse was measured.

3.2 Blood Routine Examination

After the last detection of the bleeding time, the mice were anesthetized with sodium pentobarbital, blood was collected from an abdominal cardinal vein, and indicators of blood routine examination were detected.

4. Test Results

4.1 Determination of Bleeding Time

The bleeding time of the mice in each group was shown in the table below. It can be seen from the table that compared with the control group, the bleeding time of the mice in each-dose icaritin group was significantly shortened (# indicates $P<0.05$ or ## indicates $P<0.01$), indicating that the icaritin can effectively shorten the bleeding time of the IX-knockout mice with hemophilia.

TABLE 18

Effect of icaritin on bleeding time of IX-knockout mice with hemophilia

| Groups | Number of animals | Bleeding time (min) |
|---|---|---|
| Control group (A) | 16 | 37.8 ± 12.4 |
| B | 16 | 25.5 ± 8.9# |
| C | 16 | 20.4 ± 6.9# |
| D | 16 | 16.5 ± 9.7## |

Compared with the control group,
indicates $P < 0.05$ or
indicates $P < 0.01$.

4.2 Blood Routine Examination

There was no significant difference in indicators of blood routine examination of the mice between each-dose icaritin group and the control group, indicating that the icaritin shortened the bleeding time of the mice with hemophilia and did not affect the indicators of blood routine examination.

Efficacy Example 11 Effect of Icaritin on Activated Partial Thromboplastin Time of Acquired Hemophilia A 1. Test Materials and Animals Determination of activated partial thromboplastin time: a kit was purchased from Shanghai Sun Biotech Co. Ltd. Plasma of patients with acquired hemophilia A was provided by Linyi People's Hospital. Healthy New Zealand rabbits used in the experiment were provided by China Bingfeng Animal Husbandry Cattle and Sheep Breeding Research Base.

2. Preparation of Animal Model of Acquired Hemophilia A and Administration

Twenty-four healthy New Zealand rabbits were selected and randomly divided into a control group, a model group and a treatment group with 8 rabbits in each group. Each rabbit weighed about 1.5 kg. The rabbits were fed in separate stainless steel cages at a room temperature of 18-25° C. The rabbits in each group were given a normal diet without any special treatment. One week later, the rabbit was anesthetized with 2% pentobarbital (1.5 ml/kg) via the marginal ear vein, and the left femoral vein of the rabbit was isolated and exposed for injection. The plasma of patients with acquired hemophilia A (confirmed by the Department of Hematology, Linyi People's Hospital) was intravenously injected into the 3.8% of sodium citrate (1:9) was added for anticoagulation, and the anticoagulated blood was centrifuged at 3,000 r/m to separate plasma.

3. Determination of Thromboplastin Time and Statistical Methods

Referring to the instructions of the kit, 0.1 mL of rabbit plasma was taken, 0.1 mL of a thromboplastin time reagent was added, the materials were mixed, an obtained mixture was subjected to warm bath at 37° C. for 2 min, 0.1 mL of 0.025 M calcium chloride pre-warmed at 37° C. was added, the materials were uniformly mixed, a value of thromboplastin time at each time point was measured by immediately starting a stopwatch, the thromboplastin time at each time point was repeatedly detected twice, and an average value was obtained.

The data were analyzed using an SPSS 11.0 software. The data were expressed as mean±standard deviation and subjected to a normality test and a homogeneity test of variance. Comparisons between groups were performed using a t test.

4. Test Results

The comparison of the thromboplastin time at each time point in each group was shown in Table 19. It can be seen from the table that there was no significant change in the value of the thromboplastin time of the rabbits in the control group before and after injection of plasma. In the model group, the thromboplastin time of the rabbit plasma was significantly prolonged at 30 min, 60 min, 90 min, and 120 min after the injection compared with the time point before the injection, and the prolonging of the thromboplastin time was time-dependent. The thromboplastin time at each time point can be significantly shortened in the treatment group. It showed that the icaritin can significantly shorten the activated partial thromboplastin time of patients with hemophilia and promote blood coagulation of the patients.

TABLE 19

| | | Comparison of thromboplastin time at each time point in each group | | | | |
|---|---|---|---|---|---|---|
| Groups | Number of cases (n) | −30 | 30 | 60 | 90 | 120 |
| Control group | 8 | 39.3 ± 3.76 | 38.7 ± 1.09 | 36.6 ± 2.98 | 38.3 ± 4.87 | 39.6 ± 5.98 |
| Model group | 8 | 37.6 ± 1.23 | 48.3 ± 2.09$^{\#}$ | 52.9 ± 3.44$^{\#\#}$ | 65.4 ± 3.78$^{\#\#}$ | 69.9 ± 5.23$^{\#}$ |
| Treatment group | 8 | 36.8 ± 4.12 | 40.4 ± 3.23$^{\$}$ | 39.9 ± 4.09$\$$ $ | 40.4 ± 5.67$\$ \$$ | 41.3 ± 6.21$^{\$\ \$}$ |

Note:
Compared with the control group,
$^{\#}$indicates $P < 0.05$ and $^{\#\#}$indicates $P < 0.01$;
and compared with the model group,
$^{\$}$indicates $P < 0.05$ and $^{\$\ \$}$ indicates $P < 0.01$.

rabbits in the model group and the treatment group at 2 ml/kg of rabbit body weight. The rabbits in the treatment group were immediately intragastrically administrated with icaritin at 18 mg/kg after the injection was completed and the rabbits in the model group were intragastrically administrated with a same amount of normal saline. The rabbits in the control group were intravenously injected with a same amount of normal human plasma. Blood was drawn from the marginal ear vein 30 min before and 30 min, 60 min, 90 min, and 120 min after the injection of the plasma separately,

The invention claimed is:
1. A method of preventing or treating a bleeding disorder, comprising administering a prophylactically or therapeutically effective amount of icaritin to a subject in need of such treatment, wherein the bleeding disorder is a bleeding disorder caused by platelet dysfunction, a bleeding disorder caused by vessel wall abnormalities or a bleeding disorder caused by anticoagulation and fibrinolysis abnormalities; wherein the bleeding disorder caused by the platelet dysfunction is hemorrhagic transformation after cerebral infarction, gastrointestinal bleeding caused by a thrombolytic or antithrombotic drug for cerebral infarction, or a bleeding complication of a thrombolytic or antithrombotic drug for myocardial infarction.

2. The method according to claim 1, wherein the hemorrhagic transformation after cerebral infarction is secondary, primary or asymptomatic hemorrhagic transformation after ischemic cerebral infarction.

3. The method according to claim 1, wherein in the bleeding complication of a thrombolytic or antithrombotic drug for myocardial infarction, the thrombolytic drug is selected from the group consisting of urokinase, streptokinase, reteplase, alteplase, tenecteplase and lanoteplase; the antithrombotic drug is used for antithrombotic treatment in an onset stage, and primary and secondary prevention stages of myocardial infarction; or the antithrombotic drug is one or more of an anticoagulant drug or an antiplatelet drug.

4. The method according to claim 1, wherein in the gastrointestinal bleeding caused by a thrombolytic or antithrombotic drug for cerebral infarction, the thrombolytic drug is one or more of urokinase, streptokinase, reteplase, alteplase, tenecteplase or lanoteplase; and the antithrombotic drug is one or more of an anticoagulant drug or an antiplatelet drug.

5. The method according to claim 1, wherein the platelet dysfunction is platelet activation or aggregation dysfunction.

6. The method according to claim 1, wherein the bleeding disorder caused by anticoagulation and fibrinolysis abnormalities is an acquired disease caused by factors including heparin overuse, coumarin overdose, increased immune-related anticoagulants or overdose of thrombolytic drugs.

7. The method according to claim 1, wherein icaritin is administered in a form of a pharmaceutical formulation, wherein the pharmaceutical formulation is an injection, powder for injection, a capsule, a tablet, a microemulsion, a dropping pill or an enteric soft capsule.

8. The method according to claim 1, wherein icaritin is administered at a dose of 0.01 mg/kg-100 mg/kg.

9. The method according to claim 8, wherein icaritin is administered at a dose of 0.1 mg/kg-10 mg/kg.

10. The method according to claim 2, wherein the secondary hemorrhagic transformation is caused by using one or more treatment methods of a thrombolytic drug, an antithrombotic drug and endovascular therapy.

11. The method according to claim 10, wherein the thrombolytic drug is selected from the group consisting of urokinase, streptokinase, reteplase, alteplase, tenecteplase and lanoteplase, or the antithrombotic drug is one or more of an anticoagulant drug and an antiplatelet drug.

12. The method according to claim 11, wherein the anticoagulant drug is selected from the group consisting of heparin or a pharmaceutically acceptable salt thereof, low-molecular-weight heparin or a pharmaceutically acceptable salt thereof, and recombinant hirudin.

13. The method according to claim 11, wherein the antiplatelet drug is selected from the group consisting of aspirin, clopidogrel and ticlopidine.

14. The method according to claim 2, wherein the primary hemorrhagic transformation is spontaneous hemorrhagic transformation after acute cerebral infarction.

15. The method according to claim 3, wherein the antiplatelet drug is selected from the group consisting of aspirin, clopidogrel and ticlopidine; and the anticoagulant drug is selected from the group consisting of heparin or a pharmaceutically acceptable salt thereof, low-molecular-weight heparin or a pharmaceutically acceptable salt thereof, and recombinant hirudin.

16. The method according to claim 3, wherein the bleeding complication is one or more of subcutaneous bleeding, intracranial bleeding, upper gastrointestinal bleeding or gingival bleeding.

17. The method according to claim 4, wherein the antiplatelet drug is selected from the group consisting of aspirin, clopidogrel and ticlopidine; and the anticoagulant drug is selected from the group consisting of heparin or a pharmaceutically acceptable salt thereof, low-molecular-weight heparin or a pharmaceutically acceptable salt thereof, and recombinant hirudin.

18. The method according to claim 5, wherein the platelet dysfunction is congenital platelet defect or acquired platelet defect.

19. The method according to claim 18, wherein the congenital platelet defect is hereditary giant platelet syndrome, hereditary Glanzmann thrombasthenia or congenital connective tissue disease; and the acquired platelet defect is caused by a drug or a disease.

20. The method according to claim 19, wherein the drug is one or more of an antimicrobial drug, an anti-tumor drug or heparin, and the disease is one or more of uremia, diabetes, nephrotic syndrome, coronary heart disease or leukemia.

\* \* \* \* \*